United States Patent [19]

Finkelstein et al.

[11] Patent Number: 4,677,080
[45] Date of Patent: Jun. 30, 1987

[54] RAPID PARTICLE AGGLUTINATION TEST FOR ENTEROTOXIGENIC BACTERIA

[75] Inventors: Richard A. Finkelstein; Yang Zhengshi, both of Columbia, Mo.

[73] Assignee: The Curators of the University of Missouri, Columbia, Mo.

[21] Appl. No.: 610,610

[22] Filed: May 15, 1984

[51] Int. Cl.[4] ............... G01N 33/546; G01N 33/543; G01N 33/544
[52] U.S. Cl. ........................... 436/534; 436/518; 436/528; 436/531; 436/811; 435/7; 435/253; 435/259
[58] Field of Search .................. 424/87, 88, 92; 436/501, 502, 518, 528, 531, 533, 822, 828, 811; 435/7, 253, 259

[56] References Cited

U.S. PATENT DOCUMENTS 4,533,630  8/1985  Wilkins et al. .................... 424/87 X

OTHER PUBLICATIONS

Rönnberg, B., et al., (1983), Journ. Clin. Microbiol., 17, No. 6: 1021–1025.
Honda et al., (1983), Journ. Clinical Microbiol., 17: 592–595.
Merson et al., (1980), Lancet, 2: 222–224.
Holmes et al., (1978), Infection & Immunity, 19: 101–106.
Lindholm et al., (1983), Infection & Immunity, 40: 570–576.
Remmers et al., (1982), Infection & Immunity, 37: 70–76.

*Primary Examiner*—Christine M. Nucker
*Assistant Examiner*—Jack Spiegel
*Attorney, Agent, or Firm*—Grace J. Fishel

[57] ABSTRACT

A rapid technique is disclosed for the identification of enteric bacteria which elaborate cholera-related heat-labile enterotoxin antigens which have the ability to cause diarrheal disease in man or animals. The invention includes a sensitized carrier particle for use as a reagent in an agglutination test for heat-labile enterotoxins and the use of said reagent in immunological determinations.

10 Claims, No Drawings

RAPID PARTICLE AGGLUTINATION TEST FOR ENTEROTOXIGENIC BACTERIA

The present invention relates to a rapid agglutination test for heat-labile enterotoxins.

Some enteric bacteria elaborate cholera-related heat-labile enterotoxins which are associated with their ability to cause diarrheal disease in man and animals. It has been shown that the enterotoxins of these bacteria are similar to each other immunologically, structurally and functionally.

Several different methods have been proposed for recognition of enterotoxin-producing bacteria. For the most part, these depend on biological assays in experimental animal models or in tissue cultures. In each of these instances, many colonies of the suspect bacteria must be picked and subcultured in appropriate media. Bacteria-free supernatent fluids are then prepared and tested in the respective bioassays. These methods are time-consuming, labor intensive and expensive. Methods which have been used include surgically isolated ileal loop tests in rabbits; tests in live infant mice; perfusion in rat or dog intestine; skin tests in adult rabbits and tests in cultured mouse adrenal tumor cells, Chinese hamster ovary cells or African green monkey cells. Radio-immunoassays (RIA) and enzyme-linked immunosorbant assays have also been introduced as has a radial passive immune hemolysis test which detects enterotoxin produced by colonies on the surface of an agar medium. The latter test while promising, has a severe disadvantage in that it cannot be used for testing colonies which are hemolytic and it is considerably less sensitive than the other assays. All of the other tests suffer the limitation that they require several time-consuming, expensive manipulations which involve subcultures and treatment of the specimen as well as sophisticated and expensive radioisotopes, tissue culture techniques and/or laboratory animals. In addition, the results are generally not available for at least three or four days after obtaining the specimen. The most promising test introduced recently is the Biken test which has proven to be reproducible and economical, but it also involves subculturing of the bacteria and about four days of manipulations, incubations and observations. Another method using gene-specific DNA probes provides the distinct advantage of being directly applicable to stool samples, obviating the need for a culture, but at the present time requires a radiolabeled, cloned gene probe and several days to develop autoradiograms.

The primary difficulty with all of the above tests is that they take too long to get the results such that, although they may be useful epidemiologically, they are of little or no use for directing the therapy of an individual patient. Others have been working on tests for the rapid identification of heat-labile enterotoxigenic bacteria, but insofar as known, no test is truly quick as to give results in minutes. For example a staphylococcal coagglutination test, thus far reported only with human *Escherichia coli* strains, requires an additional subculture period of 5 to 6 hours. (Honda, T., R. Samakoses, C. Sornchai, Y. Takeda and T. Miwatani. 1983. Detection by a staphylococcal coagglutination test of heat-labile enterotoxin-producing enterotoxigenic *Escherichia coli*. J. Clin. Microbiol. 17:592–595.). A variation of that test is more rapid, but gave negative results with 4 out of 43 of heat-labile enterotoxin-positive human strains and positive results with only one-third of the positive animal strains tested. (Ronnberg, B., and T. Wadstrom. 1983. Rapid detection by a coagglutination test of heat-labile enterotoxin in cell-lysates from blood agar-grown *Escherichia coli*. J. Clin. Microbiol. 17:1021–1025.). A modified enzyme-linked immunosorbent assay recently reported requires an overnight subculture onto special agar plates coated with $G_{MI}$ ganglioside and gave non-specific reactions unless particular monoclonal antibodies and corresponding rabbit anti-mouse immunoglobulin conjugate were used. (Czerkinsky, C. C., and A.-M. Svennerholm. 1983. Ganglioside $G_{MI}$ Enzyme-linked immunospot assay for simple identification of heat-labile enterotoxin-producing *Escherichia coli*. J. Clin. Microbiol. 17:965–969.).

In view of the above, there is a need for a rapid test for heat-labile enterotoxigenic bacteria, the results of which are available in minutes. It is, therefore, an object of the present invention to provide such a test which can be performed on colonies of bacteria from a primary isolation culture plate without subculturing. Other objects and features of the invention will be in part apparent and in part pointed out hereinafter, the scope of the invention being indicated by the subjoined claims.

In accordance with the present invention, microscopic carrier particles are sensitized with antibodies to the heat-labile enterotoxin to be detected. For the test to be useful, the antibody must be sufficiently specific to the heat-labile enterotoxin to be detected and present in sufficient quantities on the particles that agglutination occurs to a detectable degree when enterotoxin specifically corresponding to the antibodies on the surface of the particles is introduced into the solution with the carrier.

A number of carriers are commonly used in agglutination tests. Among these are erythrocytes, bacterial cells, bentonite and latex particles. For use in the present invention, latex particles of polystyrene are preferred and good results have been achieved when the polystyrene latex has a particle size in the range of 0.5 to 1.5 microns, more preferably in the range of 0.7 to 1.3 microns. If the particles are too small, the agglomerate is difficult to see but, on the other hand, if the particles are too large, the heat-labile enterotoxin may not be able to bind the particles together and form an agglomerate at all. At either extreme, the test is less sensitive.

In order to provide a test with high specificity and sensitivity, it is preferred that the antibodies used to sensitize the microscopic carrier particles be immunoaffinity purified to remove other antibodies and proteins otherwise present in the antisera. For example, if the antisera is not immunoaffinity purified, it may include other antibodies to other antigens previously developed by the host animal along with the desired antibody. These other antibodies and proteins may react with the bacteria to be detected giving false positives and, in general, adversely affecting the specificity and/or sensitivity of the test. The purification of heat-labile enterotoxins by immunoaffinity has been described previously (B. A. Marchlewicz and R. A. Finkelstein, Diag. Microbiol. Infect. Dis. 1983. 1:129–138.), which article is incorporated by reference herein. Basically, however, in immunoaffinity purification a pure antigen is coupled to an insoluble matrix in such a way that it retains its immunologic properties. An antiserum containing a mixture of antibodies is applied to the matrix with the insolubilized antigen and the excess washed away, leaving a new complex between the insolubilized antigen and the specific antibody to which it is coupled. This is a reversible reaction and the antibody can be separated from the antigen by changing the conditions, i.e., by lowering the pH, thus liberating the antibodies which have been purified by their immunoaffinity for a specific insolubilized antigen and which can then be concentrated and lyophilized for storage.

In preparation for the test, the microscopic carrier particles are sensitized with antibodies to the particular cholera-related heat-labile enterotoxin from bacteria suspected in the specimen. Under proper conditions of pH and ionic strength, the carrier particles will retain the antibodies without altering their immunologic ability to couple with the corresponding antigen. For example, when the carrier particles are latex they may be sensitized with antibodies in a glycine-buffered saline solution made up of 7.505 g of glycine and 5.85 g NaCl in distilled water to 1 liter, adjusted to pH 8.2 with 6N NaOH. This is shown as a specific and non-limiting example as other solutions having suitable ionic strength and pH may be made up by those skilled in the art but differing in composition according to chemicals available, personal preferences and particular carrier particles chosen.

The amount of antibody used to sensitize the carrier particles is determined empirically. For example if an insufficient amount of antibody is used, the sensitized carrier particles are theoretically highly sensitive to antigen but the agglomerate is not visible to the naked eye which is a requirement of an agglutination test. On the other hand, the test is impractically insensitive if an excess amount of antibody is used. More particularly, if the active sites on the carrier particles are filled with antibodies, there is so much competition among the particles for the antigen that the particles do not form a visible agglomerate even in the presence of a sizable amount of antigen. The optimal amount of antibody is that amount sufficient to give a visible reaction to the smallest practical amount of antigen. A typical determination of these practical limits is set forth by way of example below.

The carrier particles are not instantly sensitized with antibodies. For this purpose, it is useful to incubate the mixture during which time the carrier particles undergo brownian movement mixing with the antibodies and allowing them to react. Once equilibrium has been reached, or sufficiently closely approached, the carrier particles are preferably incubated with an inert serum protein such as bovine serum albumin to saturate the remaining active sites. This is to prevent reaction during the agglutination test with antibodies and other proteins present in the specimen which might react with antigens other than that being specifically detected thus interfering with the specificity of the test. An antibacterial preservative such as sodium azide or the like may be added to the sensitized carrier particles or they can be preserved by lyophilization.

A specimen, for example from a primary isolation culture plate, suspected to contain bacteria which elaborate cholera-related heat-labile enterotoxin is preferably pretreated to liberate the enterotoxin from the cells. This is accomplished by adding an antibiotic such as polymyxin which alters the permeability of the bacteria releasing the periplasmic proteins, including the enterotoxins. Other techniques such as osmotic shock or the like may be used to lyse the enterotoxin from the cells.

The actual test is accomplished by incubating the specimen with the sensitized carrier particles under ionic and pH conditions such that any heat-labile enterotoxin antigen corresponding to the antibodies on the surface of the particles is detected. To this end, the sample is incubated under gentle agitation allowing the sensitized carrier particles to interreact with the antigen and to interreact with each other to build up a visible macroscopic insoluble complex which indicates a positive reaction. Antibodies to heat-labile enterotoxins from one species can be used to detect heat-labile enterotoxins from another species but better sensitivity is obtained when the antibodies are homologous to the antigen being detected.

The following examples illustrate the invention.

EXAMPLE 1

Goat anti-human-enterotoxin of *Escherichia coli* (goat anti-H-LT) directed against heat-labile enterotoxin (LT) of *Escherichia coli* isolated from strain H74-114 and goat anti-porcine-enterotoxin of *Escherichia coli* (goat anti-P-LT) directed against LT isolated from strain 711/FILT were purified by immunoaffinity column chromatography for use in the following examples as follows: 10 mg samples of the pure toxin H-LT or P-LT were each coupled to approximately 1 g of cyanogen bromide-activated Sepharose 4B (Pharmacia Fine Chemicals Inc.). The corresponding goat antisera, anti-H-LT or anti-P-LT was applied to the immunoaffinity column on which the homologous toxin was coupled. Elution with 0.5M NaCl plus 0.2M glycine-HCl, pH 2.7 yielded specific homologous antibody preparations which were captured in 4 volumes of TEAN (0.05M Tris; 0.2M NaCl; 1 mM EDTA; 3 mM NaN) buffer, pH 7.9 and then concentrated by membrane ultrafiltration and lyophilized.

EXAMPLE 2

To determine the optimal concentration of antibody for sensitization of latex, latex particles were sensitized with various dilutions of anti-H-LT antiserum or immunoaffinity-purified anti-H-LT antibody from Example 1. In each instance, the antisera was diluted to the level shown in Table 1 in glycine-buffered saline solution (7.505 g of glycine and 5.85 g of NaCl in distilled water to 1 liter, adjusted to pH 8.2 with 6N NaOH) and mixed thoroughly. To samples (e.g., 200 $\mu$L) of each dilution, and equal volume of a suitable latex preparation (Bacto-Latex [0.81 micron]; Difco lot 519984 or Polysciences [1.24 micron], lot 11907) was added to this preparation and also mixed thoroughly. The sensitized latex was incubated in a water bath at 37 degrees C. for 2 h and shaken at 15-min intervals. After this, for the above-mentioned volume, 600 microliters of 0.1% bovine serum albumin (Sigma Chemical Co.) in glycine-buffered saline was added. The mixture could then be used after 30 min and was stable for 2 weeks at room temperature or at 4 degrees C. It could also be preserved by lyophilization.

The colonies of *Escherichia coli* used for testing were selected from 100 *Escherichia coli* strains for a World Health Organization study (R. G. A. Sutten, Y. Takeda and T. Miwatani (ed), Bacterial diarrheal diseases: an international symposium, in press) and provided through the generosity and courtesy of Yoshifumi Takeda and Takeshi Honda on Dorset medium. Fifty of these strains produced LT. All strains were subcultured onto MacConkey agar and meat extract agar and stored in suspensions in 2% glycerol in tryptic soy broth (Difco Laboratories) at −70 degrees C. These colonies were used for testing.

Colonies to be tested were emulsified in an Eppendorf-type microcentrifuge tube, in 30 microliter of polymyxin B-Tris NaCl buffer prepared as follows. Polymyxin B sulfate (Aerosporin; Burroughs Wellcome Co.) sterile powder was suspended in distilled water to a concentration of 100,000 U/ml; 0.5 ml of that solution was added to 2 ml of 0.1875M Tris-0.9% NaCl (pH 6.6) to yield a final solution of 20,000 U of polymyxin B per ml of 0.5M Tris-0.12M NaCl. Increasing the concentration of polymyxin B above 20,000 U/ml does not increase the sensitivity of the test. The bacterial suspension was incubated in polymyxin B-Tris-NaCl buffer at 37 degrees C. in a water bath for 5 to 30 min (a matter of convenience, depending on how many colonies were being tested) and centrifuged for 5 min in a tabletop Brinkmann Eppendorf Centrifuge 3200.

In the actual test, the results of which are shown in Table 1, 10 microliter of the colony supernatant and 5 microliter of the sensitized latex were mixed in a well of a Boerner slide (Scientific Products) or other appropriate container, e.g., ring slide (Scientific Products). The mixture was gently shaken for 3 min and then observed for agglutination by using transmitted oblique illumination. A hand lens or stereoscope was useful for interpreting weak reactions. A positive reaction was any evidence of agglutination of the latex particles, in comparison with a control, which could be observed with a naked eye, a hand lens or a stereoscope (×10 magnification). In practice, it is convenient ot record results as +++ (very strong agglutination), ++ (strong agglutination clearly visible with the naked eye), + (weak reaction visible with the naked eye but clearer with magnification) and -(no detectable reaction).

TABLE 1

| Titration of antibody for latex sensitization | | | | | | | | | |
|---|---|---|---|---|---|---|---|---|---|
| Type of antibody | Dilution of antibody | Reaction with an H-LT conc (μg/ml) of: | | | | | | | |
| | | 525 | 263 | 131 | 66 | 33 | 16.5 | 8.25 | 4.1 |
| Goat anti-H-LT antiserum | 0 | +++ | +++ | +++ | − | − | − | − | − |
| | 1:5 | − | − | − | ++ | ++ | − | − | − |
| | 1:10 | − | − | − | + | +++ | ++ | − | − |
| | 1:20 | − | − | − | − | − | ++ | ++ | − |
| Immmunopurified goat anti-H-LT antibody (a) | 0 | − | + | ++ | +++ | +++ | ++ | − | − |
| | 1:5 | − | − | − | − | + | ++ | +++ | +++ |
| | 1:10 | − | − | − | − | − | − | ++ | +++ |
| | 1:20 | − | − | − | − | − | − | ++ | +++ |
| Type of antibody | Dilution of antibody | Reaction with an H-LT conc (μg/ml) of: | | | | | | | |
| | | 2.0 | 1.0 | 0.5 | 0.25 | 0.125 | 0.06 | 0.03 | 0.015 |
| Goat anti-H-LT antiserum | 0 | − | − | − | − | − | − | − | − |
| | 1:5 | − | − | − | − | − | − | − | − |
| | 1:10 | − | − | − | − | − | − | − | − |
| | 1:20 | − | − | − | − | − | − | − | − |
| Immunopurified goat anti-H-LT antibody (a) | 0 | − | − | − | − | − | − | − | − |
| | 1:5 | ++ | + | − | − | − | − | − | − |
| | 1:10 | +++ | +++ | ++ | + | − | − | − | − |
| | 1:20 | +++ | +++ | +++ | ++ | ++ | + | + | − |

(a) 3.2 mg of protein per ml.

EXAMPLE 3

All of the data reported in Table 1 were obtained using latex from Difco (lot 519984) or latex from Polysciences, Inc. (lot 11907). As shown in Table 2, latex from different sources and having different particle sizes vary in their suitability for the rapid agglutination test of the present invention.

TABLE 2

| Suitability of various latex preparations for use in LPAT (a) | | |
|---|---|---|
| Latex type (source) | Size of particle (μm) | Minimal amt of LT detectable (μg/ml) |
| Bacto-Latex (Difco; lot 519984) | 0.81 | ≦0.5 |
| Bacto-Latex (Difco; lot 709672) | 0.81 | 2.0 |
| Polysciences (lot 11907) | 1.24 | ≦0.5 |
| Polysciences (lot 25527-red) | 1.1 | ≦0.5 |
| Polysciences (lot 24417-yellow) | 1.14 | ≦0.5 |
| Polysciences (lot 31215) | 0.32 | − (b) |
| Polysciences (lot 24550-blue) | 1.19 | − |
| Sigma (lot 21 F. 02581) | 1.091 | 2.0 |
| Sigma (lot 32 F. 05151) | 0.797 | 4.1 |
| Sigma (lot 28 C. 0051) | 0.60 | − |

(a) Latex particles were "sensitized" in the usual manner with immunopurified anti-H-LT (1:20) and then used to titrate purified H-LT as described in Table 1.
(b) —, No agglutinization at any level of H-LT.

EXAMPLE 4

The rapid agglutination test of the present invention was evaluated with bacterial colonies on different media. Table 3 summarizes results when the test was used to detect LT-producing colonies on several different commonly used enteric diagnostic culture media with and without lincomycin.

TABLE 3

| Evaluation of LPAT (a) with 100 E. coli strains on different culture media, with and without lincomycin | | |
|---|---|---|
| | | No. of strains |
| Medium | Lincomycin (b) | LPAT/Biken test    LPAT/Biken test |
| MacConkey | − | 50/50    50/50 |
| | + | 50/50    50/50 |
| EMB | − | 49/50    51/50 |
| | + | 50/50    50/50 |
| Deoxycholate-citrate | − | 50/50    50/50 |
| | + | 50/50    50/50 |

TABLE 3-continued

Evaluation of LPAT (a) with 100 *E. coli*
strains on different culture media, with and without lincomycin

| Medium | Lincomycin (b) | No. of strains LPAT/Biken test | LPAT/Biken test |
|---|---|---|---|
| Deoxycholate | − | 49/50 | 51/50 |
|  | + | 50/50 | 50/50 |
| Hektoen | − | 50/50 | 50/50 |
|  | + | 50/50 | 50/50 |
| XLD | − | 47/50 | 53/50 |
|  | + | 41/50 | 59/50 |

(a) With immunopurified antibody (1:20)
(b) Without (−) or with (+) lincomycin (90 μg/ml) in the culture medium.

EXAMPLE 5

Heat-labile producing enterotoxigenic bacteria were selected from 106 porcine *Escherichia coli* strains. It was found that purified anti-H-LT antibody and purified anti-P-LT antibody were both useful in recognizing porcine LT-producing *Escherichia coli* strains using the rapid latex agglutination test described in Example 2. The test is more sensitive, however, when homogolous reagents are used. For example, the test according to the present invention using purified anti-H-LT can detect pure H-LT at 0.03 microgram/ml whereas approximately 0.08 microgram/ml of pure P-LT was required for a positive reaction. The addition of $NaN_3$, 1% final concentration to the sensitized latex preparations does not affect the sensitivity or specificity of the test but increases the shelf-life of the sensitized latex even further.

In view of the above, it will be seen that the several objects of the invention are achieved and other advantageous results attained. As various changes could be made in the above methods and products without departing from the scope of the invention, it is intended that all matter contained in the above description shall be interpreted as illustrative and not in a limiting sense.

What is claimed is:

1. In an agglutination test, which test comprises sensitizing microscopic carrier particles with an antibody to a cholera-related heat-labile enterotoxin antigen and bringing this combination into contact with a specimen suspected to contain the corresponding antigen and observing the thus formed mixture for evidence of the formation of a macroscopic insoluble complex which indicates a positive reaction, the improvement in the method which comprises isolating colonies of the specimen from a primary culture, suspending the colonies in a medium, pretreating the colonies in the medium to liberate the enterotoxin from the cells, precipitating the cells and testing the supernatant containing the heat-labile enterotoxin liberated by the cells.

2. The method of claim 1 wherein the antibodies are immunopurified.

3. The method of claim 2 wherein the colonies isolated from the primary culture and suspended in the medium are pretreated in the medium with an antibiotic which alters the permeability of the cell walls releasing the enterotoxins.

4. The method of claim 3 wherein the antibiotic is polymyxin.

5. The method of claim 3 wherein the particles are latex and wherein the antibodies are directed to a human heat-labile enterotoxin antigen of *Escherichia coli*.

6. The method of claim 5 wherein the particles have a size in the range of about 0.5 to 1.5 micron and wherein the antibodies are immunopurified.

7. The method of claim 3 wherein the particles are latex and wherein the antibodies are directed to a porcine heat-labile enterotoxin antigen of *Escherichia coli*.

8. The method of claim 7 wherein the particles have a size in the range of about 0.5 to 1.5 micron and wherein the antibodies are immunopurified.

9. The method of claims 5 or 7 wherein the antibody is as goat antibody.

10. The method of claim 3 wherein the antibodies are homologous to the antigen to be detected.

* * * * *